United States Patent [19]

Hartig et al.

[11] Patent Number: 4,704,476

[45] Date of Patent: Nov. 3, 1987

[54] WORKING UP REACTION MIXTURES CONTAINING CYCLOHEXYL HYDRO-PEROXIDE, CYCLOHEXANOL AND CYCLOHEXANONE

[75] Inventors: Juergen Hartig, Gruenstadt; Guenter Herrmann, Heidelberg; Ekhart Lucas, Wachenheim, all of Fed. Rep. of Germany

[73] Assignee: BASF Aktiengesellschaft, Fed. Rep. of Germany

[21] Appl. No.: 3,705

[22] Filed: Jan. 15, 1987

[30] Foreign Application Priority Data

Jan. 17, 1986 [DE] Fed. Rep. of Germany ....... 3601218

[51] Int. Cl.$^4$ ............................................. C07C 45/53
[52] U.S. Cl. ...................................... 568/342; 568/835
[58] Field of Search ..................... 568/342, 835, 385

[56] References Cited

U.S. PATENT DOCUMENTS

| | | | |
|---|---|---|---|
| 2,938,924 | 5/1960 | Simon et al. | 568/342 |
| 3,923,895 | 12/1975 | Costantini et al. | 568/342 |
| 4,115,207 | 9/1978 | Murtha | 568/342 |
| 4,465,861 | 8/1984 | Hermolin | 568/342 |
| 4,499,305 | 2/1985 | Hermolin | 568/342 |
| 4,551,553 | 11/1985 | Taylor et al. | 568/342 |

FOREIGN PATENT DOCUMENTS

| | | | |
|---|---|---|---|
| 767227 | 11/1971 | Belgium | 568/342 |
| 92867 | 7/1986 | European Pat. Off. | 568/342 |
| 777087 | 6/1957 | United Kingdom | 568/342 |
| 945166 | 6/1960 | United Kingdom | 568/342 |

*Primary Examiner*—James H. Reamer
*Attorney, Agent, or Firm*—Keil & Weinkauf

[57] ABSTRACT

Reaction mixtures which contain cyclohexyl hydroperoxide, cyclohexanol and cyclohexanone and are obtained by oxidizing cyclohexane with molecular oxygen, or a gas containing this, in the liquid phase at from 130° to 200° C. under from 5 to 25 bar are worked up by treatment with an aqueous alkali solution in the presence of a cobalt salt at elevated temperatures by an improved process wherein a phosphonic acid compound of the formula

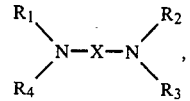

I where X is alkylene or 2 to 6 carbon atoms, $R_1$ is —CH$_2$PO$_3$H and $R_2$, $R_3$ and $R_4$ may be identical or different and are each —CH$_2$PO$_3$H, —CH$_2$OH, hydrogen or alkyl of 1 to 4 carbon atoms, is concomitantly used.

5 Claims, No Drawings

WORKING UP REACTION MIXTURES CONTAINING CYCLOHEXYL HYDRO-PEROXIDE, CYCLOHEXANOL AND CYCLOHEXANONE

In the oxidation of cyclohexane with air or oxygen under superatmospheric pressure and at elevated temperatures, mixtures of cyclohexyl hydroperoxide, cyclohexanol and cyclohexanone, other peroxides, acids and esters are obtained. To improve the yield, the cyclohexyl hydroperoxide formed is usually converted to cyclohexanol and cyclohexanone under special conditions. In many cases, the cyclohexyl hydroperoxide formed is simultaneously decomposed by adding special transition metal salts during the oxidation. For example, German Pat. No. 1,002,754 describes the oxidation and the deperoxidation with homogeneous solutions of cobalt or chromium salts. Copper and manganese salts can also be used for this purpose, as described in German Published Application DAS No. 1,193,501. However, these processes are unsatisfactory with regard to the yield. This is particularly so since substantial amounts of undesirable byproducts are formed under the conditions of the cyclohexane oxidation. European Patent Application No. 92,867 furthermore discloses a process in which the decomposition of cyclohexyl hydroperoxide in cyclohexane oxidation mixtures is effected by the addition of an alkali containing cobalt salts at 110° C. The waste liquors obtained in this procedure cannot be used again and have to be disposed of.

It is an object of the present invention to carry out the decomposition of cyclohexyl hydroperoxide in such a way that a very small amount of byproducts is formed, decomposition takes place rapidly at a very low temperature, no deposits are produced and furthermore the waste liquor obtained is reused industrially.

We have found that this object is achieved by a process for working up reaction mixtures which contain cyclohexyl hydroperoxide, cyclohexanol and cyclohexanone and are obtained by oxidizing cyclohexane with molecular oxygen, or a gas containing this, in the liquid phase at from 130° to 200° C. and under from 5 to 25 bar by treatment with an aqueous alkali solution in the presence of a cobalt salt at elevated temperatures, wherein a phosphonic acid compound of the formula

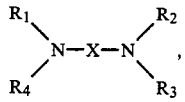

where X is alkylene of 2 to 6 carbon atoms and $R_1$ is $-CH_2PO_3H$ and $R_2$, $R_3$ and $R_4$ may be identical or different and are each $-CH_2PO_3H$, $-CH_2OH$, hydrogen or alkyl of 1 to 4 carbon atoms, is concomitantly used.

The novel process has the advantages that the selective decomposition of the cyclohexyl hydroperoxide to cyclohexanol and cyclohexanone takes place rapidly at a relatively low temperature, a small amount of byproducts is formed and no deposits are produced, and, finally, it is possible to use alkali metal carbonate solutions which can be worked up again in a simple manner and recycled to the process.

According to the invention, a reaction mixture containing cyclohexyl hydroperoxide, cyclohexanol and cyclohexanone is used as the starting material, the said mixture being obtained by oxidation of cyclohexane with molecular oxygen, or a gas containing this, eg. air, in the liquid phase at from 130° to 200° C. and advantageously under from 5 to 25 bar. Such mixtures contain, as a rule, from 0.5 to 10% by weight of cyclohexyl hydroperoxide. Advantageously, the reaction mixtures thus obtained are washed with water or an alkali solution before being further treated. Typical reaction mixtures contain, in addition to cyclohexane, from 1 to 7% by weight of cyclohexanone and cyclohexanol and from 0.5 to 3.5% by weight of cyclohexyl hydroperoxide, as well as byproducts such as esters, carboxylic acids and possibly water, for example in an amount of up to 2% by weight. Suitable reaction mixtures are obtained, for example, by the method described in German Pat. No. 1,046,610.

The reaction mixture is treated with an aqueous alkali solution, for example a solution of sodium hydroxide or potassium hydroxide or the corresponding carbonates. If an alkali metal hydroxide solution is used, 5-50, in particular 20-30, % strength by weight aqueous solutions are advantageous. Where alkali metal carbonate solutions are employed, they are used in the form of 5-30, in particular 20-25, % strength by weight aqueous solutions. Sodium carbonate is particularly preferably used. As a rule, from 3 to 10 g of the alkali metal hydroxide or carbonate in the form of an aqueous solution are used per kg of reaction mixture.

The treatment is carried out in the presence of a cobalt salt, preferably a water-soluble cobalt salt. Advantageous salts are water-soluble nitrates or sulfates, in particular salts of lower fatty acids, such as acetates. The stated cobalt salts are advantageously used in an amount of from 0.1 to 1000 ppm, in particular from 1 to 100 ppm, calculated as cobalt and based on the aqueous alkali solution.

An essential feature of the invention is that, in addition, the reaction is carried out in the presence of a phosphonic acid of the formula

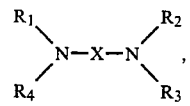

where X is alkylene of 2 to 6 carbon atoms, $R_1$ is $-CH_2PO_3H$ and $R_2$, $R_3$ and $R_4$ may be identical or different and are each $-CH_2PO_3H$, $-CH_2OH$, hydrogen or alkyl of 1 to 4 carbon atoms. Examples of suitable compounds are ethylenediaminetetramethylenephosphonic acid, 1,3-propylenediaminetetramethylenephosphonic acid, 1,4-butylenediaminetetramethylenephosphonic acid, ethylenediaminedimethyldimethylenephosphonic acid, 1,3-propylenediaminedimethyldimethylenephosphonic acid and ethylenediaminemethyltrimethylenephosphonic acid. Ethylenediaminetetramethylenephosphonic acid and 1,3-propylenediaminetetramethylenephosphonic acid are particularly preferred. The alkylene radical X may be straight-chain or branched and is preferably of 2 or 3 carbon atoms.

Phosphonic acids of the formula I are preferably used in an amount such that the concomitantly used metal compounds are present as soluble complexes in the aqueous alkali solution. It has proven useful to use the compounds of the formula I in amounts of from 10 to 2000 ppm, based on the aqueous alkali solution.

The treatment is advantageously carried out at from 50° to 150° C., in particular from 80° to 120° C. The pressure employed is, for example, from 1 to 50 bar and advantageously depends on the temperature used. The treatment of the cyclohexane oxidation mixture is advantageously effected by the cocurrent or countercurrent method, particularly preferably by the cocurrent method. The duration of treatment is as a rule from 2 to 60 minutes. When the treatment is complete, the aqueous alkali solution is separated off by a conventional method, for example decantation, cyclohexane is distilled off from the organic phase and cyclohexanol and cyclohexanone are obtained. The cyclohexane recovered is recycled to the oxidation. The resulting aqueous waste liquor, which, in addition to alkali, contains dissolved alkali metal salts of lower fatty acids, is advantageously incinerated and an alkali metal carbonate recovered. This procedure has proven particularly useful where sodium carbonate is used. The sodium carbonate obtained during the incineration can be reused in the form of an aqueous solution for the novel treatment of oxidation mixtures from the oxidation of cyclohexane. The disposal of waste liquors requiring treatment is thus dispensed with.

Cyclohexanol and cyclohexanone are important starting compounds for fiber raw materials, such as adipic acid or caprolactam.

The Examples which follow illustrate the process according to the invention.

EXAMPLE 1

100 g of a cyclohexane oxidation mixture which, in addition to cyclohexane, contains 1.7% by weight of cyclohexanol, 0.3% by weight of cyclohexanone, 1.2% by weight of cyclohexyl hydroperoxide and byproducts is heated for one hour at 80° C., while stirring, with 100 g of a 20% strength by weight sodium carbonate solution which contains 0.13 g of ethylenediaminetetramethylenephosphonic acid and 5 mg of cobalt as cobalt acetate in the form of a solution. After the treatment, all of the cyclohexyl hydroperoxide is found to have decomposed.

EXAMPLE 2

A cyclohexane oxidation mixture which, in addition to cyclohexane, contains 1.7% by weight of cyclohexanol, 0.9% by weight of cyclohexanone, 1.2% by weight of cyclohexyl hydroperoxide and byproducts, and a 10% strength by weight sodium carbonate solution which contains 25 ppm of cobalt in the form of a complex with ethylenediaminetetramethylenephosphonic acid are fed, by the cocurrent method and at 75° C., into a 2 m long pulsed sieve tray column which can be heated externally and has an internal diameter of 25 mm. 1 l/h of the oxidation mixture and 0.2 l/h of sodium carbonate solution are introduced. The residence time is 50 minutes. After separation into an organic phase and an aqueous phase, the former is separated off and analyzed. The cyclohexyl hydroperoxide present in the organic phase is found to have undergone 95–98% conversion.

COMPARATIVE EXAMPLE 1

The procedure described in Example 1 is followed, except that only 100 g of 20% strength by weight sodium carbonate solution are used, the said solution containing only 5 mg of cobalt acetate, calculated as cobalt. The process is otherwise carried out as described in Example 1. Analysis of the cyclohexane oxidation mixture treated in this manner shows that less than 2% of the cyclohexyl hydroperoxide has been decomposed.

COMPARATIVE EXAMPLE 2

The procedure described in Example 1 is followed, and
(a) 100 g of 20% strength by weight sodium carbonate solution containing 1000 ppm of vanadium as vanadium pentoxide,
(b) 1000 ppm of cobalt as sodium hexanitrocobaltate, and
(c) 1000 ppm of chromium as chromium trioxide
are used in 3 separate batches.

After a procedure similar to that described in Example 1, the decomposition of the cyclohexyl hydroperoxide is determined. This is <2% in (a), in (b) and in (c).

We claim:

1. In a process for working up a reaction mixture which contains cyclohexyl hydroperoxide, cyclohexanol and cyclohexanone and is obtained by oxidizing cyclohexane with molecular oxygen, or a gas containing this, in the liquid phase at from 130° to 200° C. and under from 5 to 25 bar, by treatment with an aqueous alkali solution in the presence of a cobalt salt at elevated temperatures, the improvement that a phosphonic acid compound of the formula

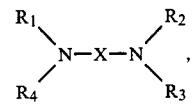

where X is alkylene of 2 to 6 carbon atoms, $R_1$ is —$CH_2PO_3H$ and $R_2$, $R_3$ and $R_4$ may be identical or different and are each —$CH_2PO_3H$, —$CH_2OH$, hydrogen or alkyl of 1 to 4 carbon atoms, is concomitantly used.

2. A process as claimed in claim 1, wherein a water-soluble cobalt salt is concomitantly used.

3. A process as claimed in claim 1, wherein ethylenediaminetetramethylenephosphonic acid is used.

4. A process as claimed in claim 1, wherein an aqueous sodium carbonate solution is used.

5. A process as claimed in claim 1, wherein the waste liquor is separated off after treatment and incinerated, and the sodium carbonate thus obtained is reused as an aqueous solution for the treatment of cyclohexane oxidation mixtures.

* * * * *